(12) United States Patent
Nielsen et al.

(10) Patent No.: US 11,026,614 B2
(45) Date of Patent: Jun. 8, 2021

(54) PRESSURE SENSOR

(71) Applicant: Auckland UniServices Limited, Auckland (NZ)

(72) Inventors: Poul Michael Fonss Nielsen, Epsom (NZ); Jennifer Ann Kruger, Mairangi Bay (NZ); David Mortimer Budgett, Pt Chevalier (NZ); Andrew James Taberner, Mt Eden (NZ); John Daniel McCormick, Oneroa (NZ)

(73) Assignee: Aukland UniServices Limited, Auckland (NZ)

( * ) Notice: Subject to any disclaimer, the term of this patent is extended or adjusted under 35 U.S.C. 154(b) by 188 days.

(21) Appl. No.: 15/736,682

(22) PCT Filed: Jun. 15, 2016

(86) PCT No.: PCT/NZ2016/050097
§ 371 (c)(1),
(2) Date: Dec. 14, 2017

(87) PCT Pub. No.: WO2016/204631
PCT Pub. Date: Dec. 22, 2016

(65) Prior Publication Data
US 2018/0214063 A1   Aug. 2, 2018

(30) Foreign Application Priority Data

Jun. 15, 2015 (NZ) .......................... 709117

(51) Int. Cl.
*A61B 5/00* (2006.01)
*A61B 5/20* (2006.01)
*A61B 5/03* (2006.01)

(52) U.S. Cl.
CPC .............. *A61B 5/205* (2013.01); *A61B 5/002* (2013.01); *A61B 5/036* (2013.01); *A61B 5/4337* (2013.01);
(Continued)

(58) Field of Classification Search
None
See application file for complete search history.

(56) References Cited

U.S. PATENT DOCUMENTS

| 4,873,990 A | 10/1989 | Holmes et al. |
| 5,433,216 A | 7/1995 | Sugrue et al. |

(Continued)

FOREIGN PATENT DOCUMENTS

| WO | WO-2005025415 | 3/2005 |
| WO | WO-2016204631 | 12/2016 |

OTHER PUBLICATIONS

"International Application No. PCT/NZ2016/050097, International Preliminary Report on Patentability dated Sep. 7, 2016", (Sep. 7, 2016), 9 pgs.

(Continued)

*Primary Examiner* — Michael R Bloch
(74) *Attorney, Agent, or Firm* — Schwegman Lundber & Woessner, P.A.

(57) ABSTRACT

A pressure sensor apparatus includes: a plurality of pressure responsive chambers provided along a longitudinal dimension of the apparatus, and a pressure sensor device provided in each chamber which together provide a pressure profile in an anatomical cavity.

23 Claims, 10 Drawing Sheets

(52) U.S. Cl.
CPC ............. *A61B 5/486* (2013.01); *A61B 5/6879* (2013.01); *A61B 2562/0247* (2013.01); *A61B 2562/043* (2013.01); *A61B 2562/164* (2013.01); *A61B 2562/168* (2013.01)

(56) References Cited

U.S. PATENT DOCUMENTS

| | | | |
|---|---|---|---|
| 6,264,612 B1 * | 7/2001 | McConnell | A61B 5/036 600/485 |
| 2009/0069714 A1 | 3/2009 | Eichmann et al. | |
| 2009/0082698 A1 | 3/2009 | Kassab | |
| 2013/0130871 A1 * | 5/2013 | McCoy | A63B 23/20 482/113 |
| 2015/0032030 A1 * | 1/2015 | Iglesias | A61B 5/103 600/587 |
| 2015/0196802 A1 * | 7/2015 | Siegel | A63B 21/0023 482/8 |

OTHER PUBLICATIONS

"International Application No. PCT/NZ2016/050097, International Search Report and Written Opinion dated Sep. 7, 2016", (Sep. 7, 2016), 16 pgs.

* cited by examiner

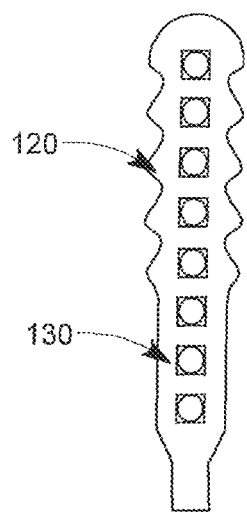 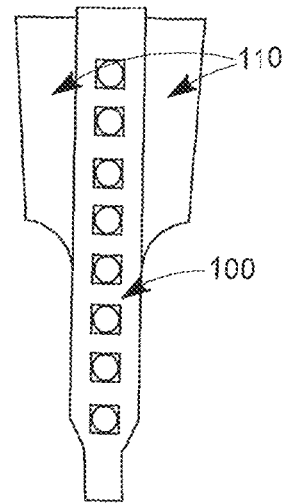
FIG. 12a  FIG. 12b
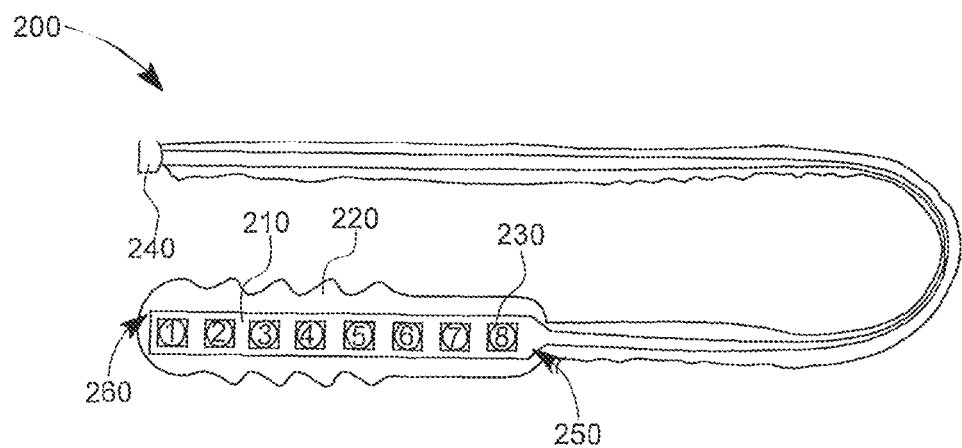
FIG. 13

PRESSURE SENSOR

PRIORITY CLAIM TO RELATED APPLICATIONS

This application is a U.S. national stage application filed under 35 U.S.C. § 371 from International Application Serial No. PCT/NZ2016/050097, which was filed 15 Jun. 2016, and published as WO2016/204631 on 22 Dec. 2016, and which claims priority to New Zealand Application No. 709117, filed 15 Jun. 2015, which applications and publication are incorporated by reference as if reproduced herein and made a part hereof in their entirety, and the benefit of priority of each of which is claimed herein.

FIELD OF THE INVENTION

The present invention relates to pressure sensors and in particular to pressure sensors that can be placed inside a human body. The pressure sensor preferably measures a pressure profile along a vaginal cavity, measuring both the intra-abdominal pressure and pelvic floor pressure.

BACKGROUND

There has been increasing interest in quantitatively investigating the association between abdominal pressure related to exercise and the development of urinary incontinence and pelvic organ prolapse (POP). Although it is well recognised that regular, moderate to intense exercise is important for health and well-being, current recommendations for women either at risk of incontinence, POP, or post-surgery, are inconsistent and variable. It is assumed that an increase in IAP may adversely affect the support structures of the pelvic organs or the integrity of the surgical repair. However, there is little evidence-based information to support these assumptions.

The aetiology of POP and urinary incontinence is multifactorial, but ultimately related to the inability of the pelvic support systems to counteract pressure exerted by the abdominal contents, resulting in descent of the pelvic organs. Epidemiological studies suggest that women are more likely to present with POP if they suffer from chronic cough, constipation, have a high body mass index, or undertake repeated heavy lifting.

Abdominal pressure is generated by the gravitational loading of the abdominal contents, which are relatively incompressible. Therefore, in accordance with Pascal's Law, the measurement of IAP in one location can be assumed to represent the pressure throughout the abdomen, ignoring hydrostatic loading. Whilst the International Continence Society refers to abdominal pressure ($P_{abd}$), as that which surrounds the bladder in the context of urodynamics, for the purposes of this patent application we will use the term intra-abdominal pressure (IAP).

Thus, the measurement of IAP is commonly performed using either an intra-vesical (i.e., bladder) or intra-rectal pressure transducer, or a rectal transducer placed intra-vaginally. Using these devices, pressures are measured using fluid-filled systems, which use the fluid to physically pass the pressure indication externally of the body. Thus the patient is connected to a pressure measuring and recording device which measures the pressure of the fluid. Pressure wave dampening and fluid inertia associated with fluid-filled systems are likely to cause artefacts that will decrease the sensitivity of measurement of pressure. Additionally, movement of the tubing itself will cause significant inaccuracies that can be of similar magnitude to the IAP being measured. These issues, and the low data sampling rates of current commercial systems, make assessment of change in IAP during exercise difficult. Several studies that have used commercially available urodynamics systems to measure increases in IAP during exercise have been limited by the factors mentioned above, as well as by retention issues of the pressure sensor. In most studies, movements were restricted to exercises that could be performed whilst connected to the urodynamics system, again limiting the kind of exercise that could be assessed.

OBJECTS OF THE INVENTION

It is an object of the invention to provide a pressure sensor which will at least go some way to overcoming disadvantages of existing systems, or which will at least provide a useful alternative to existing systems.

Further objects of the invention will become apparent from the following description.

SUMMARY OF INVENTION

Accordingly in one aspect the invention may broadly be said to consist in a pressure sensor apparatus comprising:

a plurality of pressure responsive chambers provided along a first dimension of the apparatus; and a pressure sensor device provided in each chamber.

Preferably the chambers are arranged successively along the first dimension such that the apparatus may simultaneously sense pressure to thereby sense a pressure profile along the first dimension.

Preferably each chamber comprises at least one pressure transmitting wall.

Preferably mechanical isolation means is provided between the chambers. In one embodiment the mechanical isolation means comprises a pressure resistant barrier between adjacent chambers. Preferably the pressure resistant barrier is sufficient to substantially prevent pressure changes in one chamber affecting pressure in the adjacent chamber.

Preferably each chamber is filled with fluid. Preferably the pressure sensor device senses the pressure of the fluid in the chamber. In one embodiment the fluid comprises air.

Preferably the apparatus further comprises a data transfer means, such as a transmission means to transmit the sensed pressure from each sensor to a further apparatus. In one embodiment the further apparatus may comprise one or more of a measurement, storage, or display apparatus.

In one embodiment the transmission means is provided distally from the plurality of chambers. In another embodiment the transmission means may be located proximally to the plurality of chambers.

Preferably the apparatus further comprises a retention means. In one embodiment the retention means comprises a retention contour which may extend in a second dimension which is substantially transverse to the first dimension. The retention means may be a contour provided as one or more ribs or wings dependent from the apparatus.

Preferably the apparatus includes an exit or funnel means. This may comprise a data exit port, and/or support a tube or conduit within which conductors may be located.

Preferably the apparatus comprises an intra-abdominal pressure sensing device.

Preferably the apparatus comprises an intra-vaginal device.

In another aspect the invention may broadly be said to consist in an intra-vaginal pressure sensor apparatus comprising:

a plurality of pressure sensors provided along a first dimension of the apparatus whereby a pressure profile can be determined along the first dimension.

Preferably each pressure sensor device is provided in a chamber.

Preferably the chambers are arranged successively along the first dimension such that in use the apparatus may sense a pressure profile along the vagina.

Preferably each chamber comprises at least one pressure transmitting wall.

Preferably mechanical isolation means is provided between the chambers. In one embodiment the mechanical isolation means comprises a pressure resistant pathway between adjacent chambers. Preferably the pressure resistant pathway is sufficient to substantially prevent pressure changes in one chamber affecting pressure in the adjacent chamber.

Preferably each chamber is filled with fluid. Preferably the pressure sensor device senses the pressure of the fluid in the chamber. In one embodiment the fluid comprises air.

Preferably the apparatus further comprises a transmission means to transmit the sensed pressure from each sensor to a further apparatus. In one embodiment the further apparatus may comprise one or more of a measurement, storage, or display apparatus.

In one embodiment the transmission means is provided distally from the plurality of chambers. In another embodiment the transmission means may be located proximally to the plurality of chambers.

Preferably the apparatus further comprises a retention means. In one embodiment the retention means extends in a second dimension which is substantially transverse to the first dimension. The retention means may be provided as one or more ribs or wings dependent from the apparatus.

Preferably the apparatus includes an exit or funnel means. This may comprise a data exit port, and/or support a tube or conduit within which conductors may be located.

In another aspect the invention may broadly be said to consist in a method of providing a pressure sensor apparatus, the method comprising:

providing a first part structure with a plurality of recesses;
providing a second part structure;
providing a pressure sensing device in each recess, and;
joining the part structures to thereby close the recesses and form a plurality of pressure responsive chambers.

Preferably the chambers are provided along a first dimension of the apparatus.

Preferably the part structures are flexible.

Preferably at least one of the part structures comprises a pressure transmitting material.

Preferably the method includes filling each chamber with fluid.

Preferably the step of filling each chamber with fluid occurs prior to joining the part structures.

Preferably the pressure sensor device senses the pressure of the fluid in the chamber. In one embodiment the fluid comprises air.

In another aspect the invention may broadly be said to consist in a method of providing a pressure sensor apparatus, the method comprising:

providing a substructure with a plurality of recesses or openings;
providing a pressure sensing device in each recess or opening, and;
closing the recesses or openings with a pressure transmitting material to form a plurality of pressure responsive chambers.

Preferably the recesses or openings are provided along a first dimension of the substructure.

Preferably the substructure is flexible.

Preferably the pressure transmitting material is flexible.

Preferably the step of closing the recesses or openings comprises overmoulding the substructure.

Preferably the method includes filling each chamber with fluid. Preferably the pressure sensor device senses the pressure of the fluid in the chamber. In one embodiment the fluid comprises air.

In a further aspect, the invention broadly provides a method of measuring pressure in an anatomical cavity comprising simultaneously sensing pressure at a plurality of locations along a first dimension of the cavity and recording the sensed pressure measurements to provide a pressure profile.

Further aspects of the invention will become apparent from the following description.

DRAWING DESCRIPTION

A number of embodiments of the invention will now be described by way of example with reference to the following drawings.

FIG. 12(a) shows an embodiment of a pressure sensor apparatus.

FIG. 12(b) shows another embodiment of a pressure sensor apparatus.

FIG. 13 shows an embodiment of a pressor sensor apparatus having eight pressure sensors.

DETAILED DESCRIPTION OF THE DRAWINGS

Figure 1:
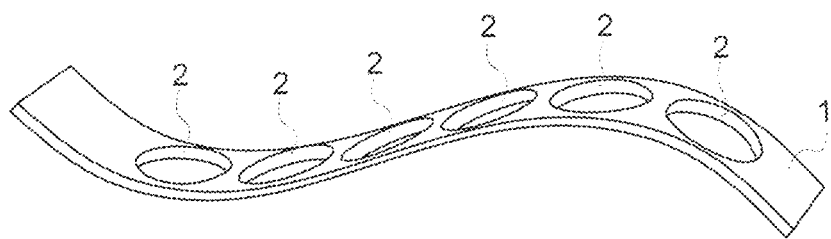
FIG. 1 is an isometric view of a flexible substrate which may be used to form apparatus according to the invention.

Throughout the description like reference numerals will be used to refer to like features in different embodiments.

Pelvic floor disorders, such as stress urinary incontinence (SUI) and pelvic organ prolapse (POP), are distressing and cost-intensive conditions that affect more than 25% of the female population. Although the exact mechanisms of POP and SUI are poorly understood, the development of such conditions are likely to alter the pressures acting on the vaginal wall, and thus change the vaginal pressure profile. There is little research on the change in the vaginal pressure profile in response to either surgical correction of POP or as a consequence of pelvic floor muscle training. Recent reviews suggest that pelvic floor muscle training (PFMT) is an effective first line treatment for women with stress urinary incontinence, and mild POP. However, more than 30% of women are unable to effectively contract their pelvic floor muscles and PFMT is contingent on the exercises being performed correctly. When these exercises are correctly performed, there is an increased pressure in the region of the pelvic floor muscles, while keeping abdominal pressure low.

The apparatus disclosed herein allows pressure within a mamallian body, in particular a human body to be sensed. The apparatus has particular application to sensing intra-abdominal pressure to provide an indication or quantification of muscle activity. Approximately 30% of women in developed countries suffer from urinary incontinence and mild pelvic organ prolapse. Pelvic floor muscle (PFM) exercises are effective in the prevention and treatment of these dysfunctions. To advise women on suitable exercises and to control whether these exercises are performed correctly, PFM strength and abdominal pressure need to be assessed.

Additionally, after surgery, such as anterior vaginal repair or the like, the pressure sensor of the present invention could provide feedback on the outcomes of the surgery.

In the following description the application of the pressure sensor of the present invention is to intra-abdominal pressure and use of the sensor within the vaginal cavity. However, the pressure sensor of the present invention could be used in any other body or anatomical cavity, such as, the anus, urinary tract, bowels or the like, to measure pressures.

The pressure sensor of the present invention is preferably a compliant intra-vaginal pressure sensing device that is able to record the vaginal pressure profile at rest, during PFMT and everyday activities. As a result vaginal pressure profiles may be used as biofeedback for PFMT, being able to measure both abdominal and pelvic floor (PF) pressure simultaneously, in addition to assessing the vaginal pressure profile pre- and post-surgery.

Additionally, the quantification of pelvic floor pressure and pressure profiles will provide measurements of pelvic floor and abdominal pressure to help identify women at risk of Pelvic Prolapse or Urinary Incontinence. Such an apparatus may also be used by physiotherapists and health providers to ensure pelvic floor exercises are being performed correctly Referring to FIG. 1, a flexible substructure 1 is shown, which comprises a first part of a pressure sensor apparatus. The substructure 1 may be formed from a relatively inert flexible material such as silicone or a material having similar properties. For example, a biocompatible silicone (e.g. MED-4960) may be used. The substructure 1 has a number of openings 2 which may be used to house pressure sensor devices as will be described further below. To complete the apparatus, the substructure 1 has a membrane attached to or moulded about either side, so that the openings 2 become chambers within which individual pressure sensing devices are housed. The material from which the membranes are formed (for example a silicone or similar material) allows pressure to be transmitted from the environment in which the apparatus is located into the chamber. Thus the sensing devices are independently isolated in separate chambers. The chambers are designed to be substantially mechanically isolated from each other. For example, the pathway or wall regions between adjacent chambers are selected to provide a pressure resistant barrier or pathway between adjacent chambers. Preferably the barrier provides mechanical isolation which is sufficient to substantially prevent pressure changes in one chamber affecting pressure in the adjacent chamber. The mechanical isolation between chambers results in only a small change in pressure in each chamber when the array is bent compared to the magnitude of the pressure changes during a pelvic floor exercise. In a preferred embodiment a fluid such as air is present in each chamber, and the sensing devices detect or sense the pressure of this fluid.

Figure 2:
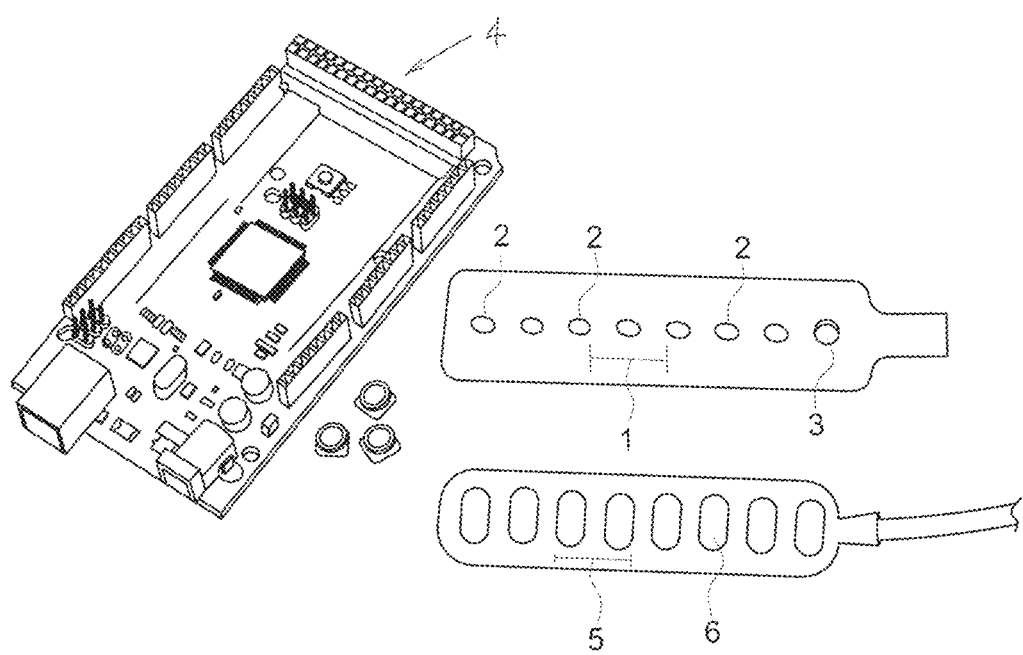
FIG. 2 is a photograph showing two partially complete embodiments according to the invention, together with a processing apparatus.
Figure 9:
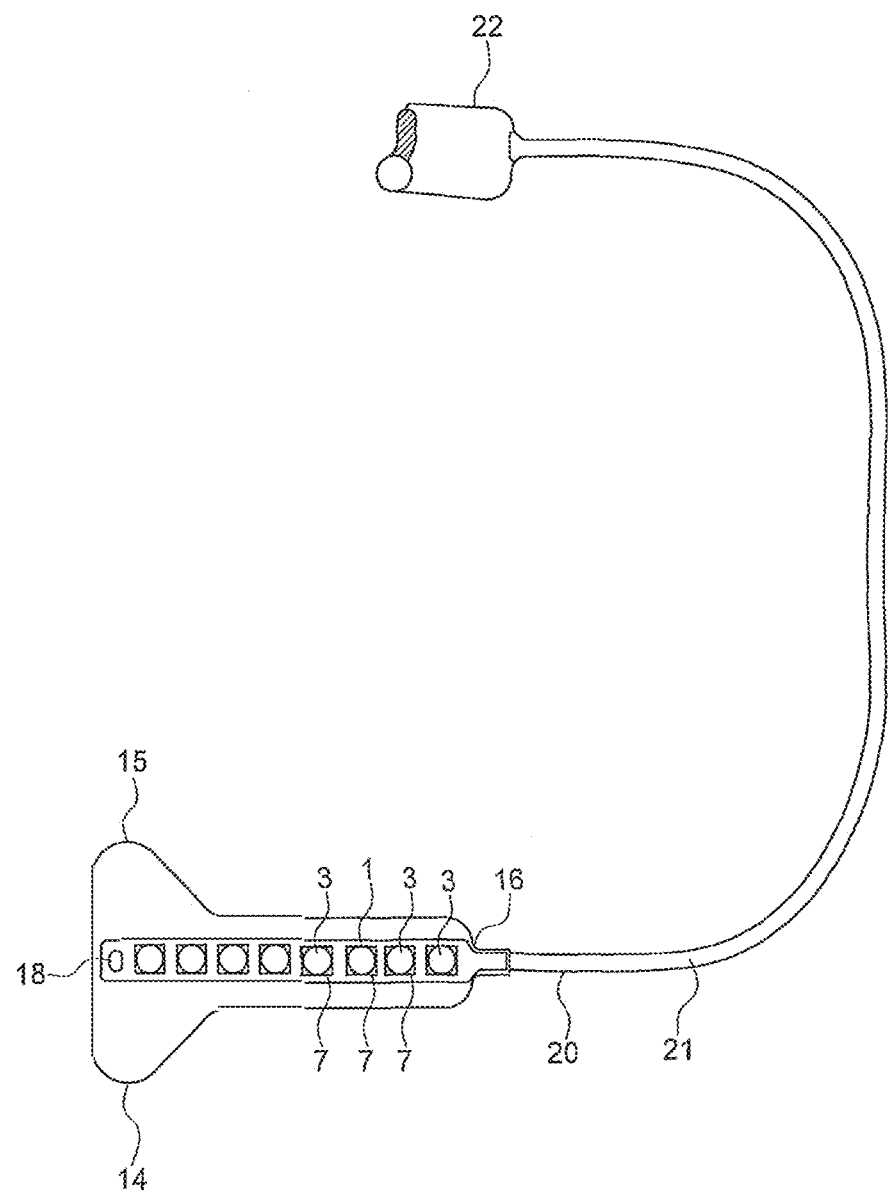
FIG. 9 is a drawing showing an embodiment ready for use.

Turning now to FIG. 2, another embodiment of substrate 1 is shown, including a pressure sensing device 3. In this example the pressure sensing device comprises a MS5803-02BA pressure sensor, for connection to a processing/measuring device 4 comprising an Arduino Mega 2560 board. A smaller processing/measuring device 22 is shown in FIG. 9 and is based on the Bluetooth Smart nRF51822 system on a chip from Nordic Semiconductor. Returning to FIG. 2, to complete the apparatus, the substructure 1 has a membrane attached to the upper side covering over the openings 2 that contain the sensing device 3. Another substructure embodiment 5 is shown having pockets 6 rather than openings 2 for receiving the pressure sensing devices 3. The substructure 5 includes a membrane which is fabricated in the single moulding process. The substrate 5 has a membrane in the top side and a second membrane in the bottom side and the pressure sensing device will respond to pressure on either membrane.

When the substructure is fully assembled the pockets 5 become chambers within which individual pressure sensing devices are housed. Again, the material from which the membranes are formed (and/or the material from which the substructure 5 is formed) allows pressure to be transmitted from the environment in which the apparatus is located into the completed chamber, that the pressure sensing device 3 that is housed in each chamber can sense the pressure in the immediate environment, for example the pressure at a location in an anatomical cavity in which the assembled apparatus is located.

Although the examples discussed in FIG. 2 are designed to provide eight chambers (i.e. eight pressure sensing devices), a greater or lesser number of chambers may be provided. In some embodiments six chambers are provided. It will be seen that the assembled apparatus is substantially elongate i.e. a first (length) dimension is greater than a second transverse (width) dimension. The chambers are arranged successively along the first dimension which in this example is a longitudinal dimension of the apparatus. The array or row of chambers provided along the first dimension allows pressure measurements to be sensed or recorded simultaneously by the sensing devices to thus allow a pressure profile to be sensed or measured along that dimension. The chambers do not have to be arranged in a line as shown in the drawings.

Figure 3:
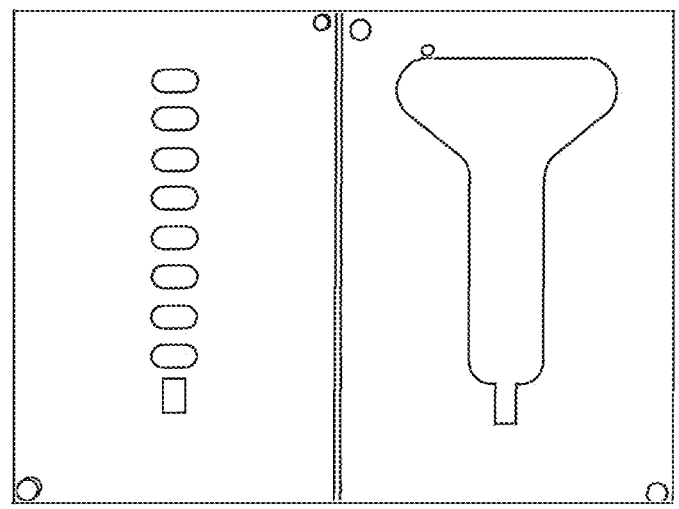
FIG. 3 is a photograph showing moulds for forming another embodiment according to the invention.
Figure 4:
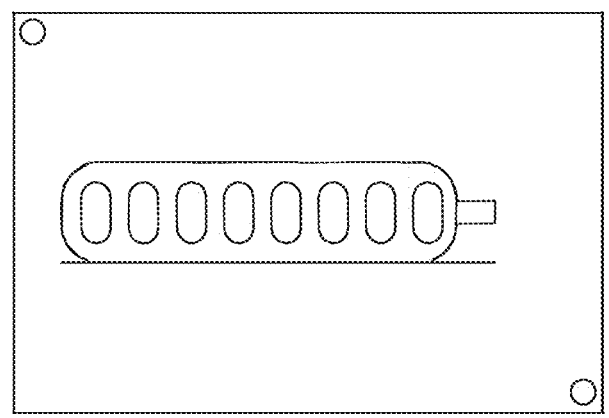
FIG. 4 is a drawing of one of the moulds shown in FIG. 3.
Figure 5:
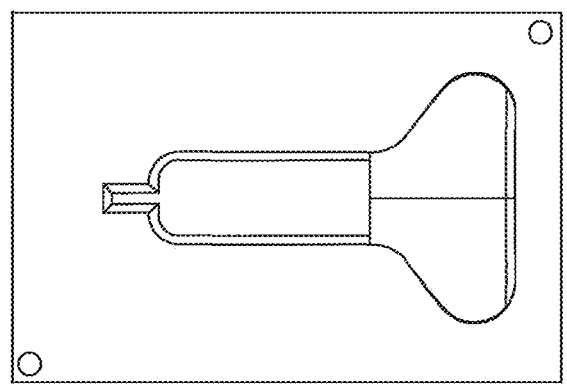
FIG. 5 is a drawing of other of the moulds shown in FIG. 3.

In FIG. 3, two aluminium moulds 10, 11 are provided for another embodiment, or for moulding over the substructures referred to above, are shown. Each mould is seen more clearly in FIGS. 4 and 5. The moulds allow the apparatus to be injection moulded using a biocompatible silicone (e.g. MED-4960).

The mouldable material may be provided in mould 11, and then mould 10 is located (face down) over 11 so that one half of a resultant structure is provided. The process is repeated to form the other half structure. The sensing devices can then be placed in the recesses formed in a first half. The second half is then bonded to the first half, thereby closing the recesses to from chambers that contain the sensing devices.

As will be described further below, this example includes a retention means or contour formed by one or more external regions of the apparatus, and an exit interface in the form or a funnel portion 16. A similar example is shown in FIG. 7, the primary differences between the embodiments being that the FIG. 7 embodiment has chambers with a substantially square shape in plan view (whereas those in the FIG. 3, 4, 5 embodiment are a rounded rectangular shape), and the FIG. 7 embodiment includes an insertion means in the form of aperture 18 which may be used with an applicator to insert the device.

Figure 6:
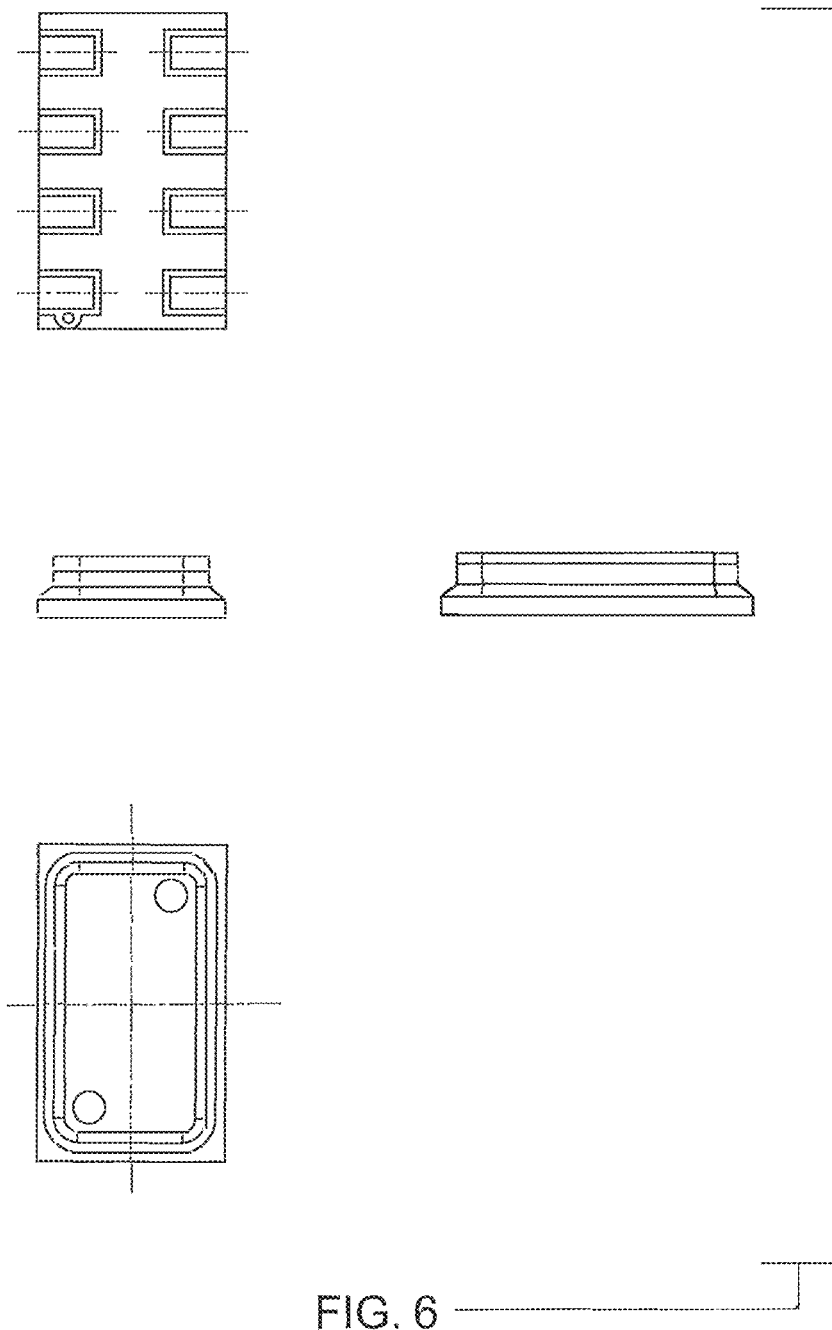
FIG. 6 shows the package outline and pin configuration of a pressure sensor for use with the embodiments shown in FIGS. 3 and 4.

A sensing device (in this example a MS5611-01BA sensor) of the form shown in FIG. 6 may be used with the FIG. 3, 4, 5 embodiment. The MS5611-01BA sensor is a high resolution altimeter sensor from MEAS Switzerland with SPI and I2C bus interface. This barometric pressure sensor is optimized for altimeters and variometers with an altitude resolution of 10 cm. The sensor module includes a high linearity pressure sensor and an ultra-low power 24 bit ΔΣ ADC with internal factory calibrated coefficients. The MS5611-01 BA can be interfaced to many different microcontrollers. The communication protocol is simple, without the need of programming internal registers in the device. Small dimensions of only 5.0 mm×3.0 mm and a height of only 1.0 mm allow for integration in mobile devices.

Figure 7:
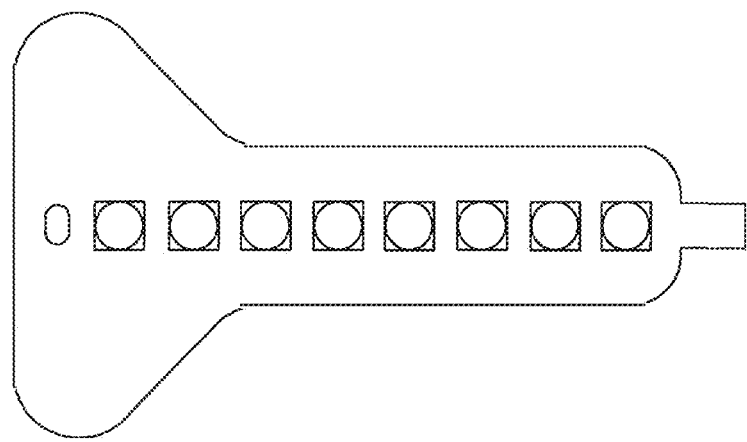
FIG. 7 is a drawing of a further embodiment of apparatus according to the invention.
Figure 8:
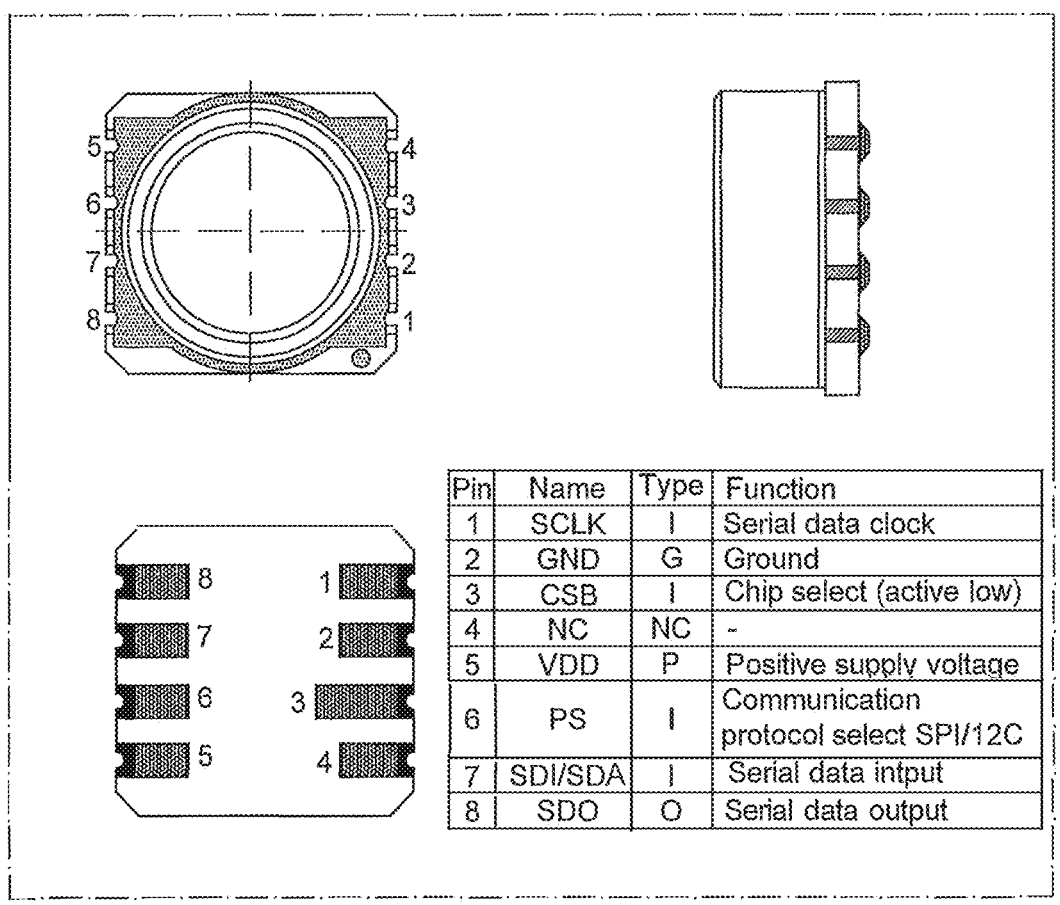
FIG. 8 shows the package outline and pin configuration of a pressure sensor for use with the embodiment shown in FIG. 7.

A sensing device (in this example a MS5803-01 BA pressure sensor) of the form shown in FIG. 8 may be used with the FIG. 7 embodiment. The MS5803-01 BA sensor is a high resolution altimeter sensor from Measurement Specialties with SPI and I2C bus interface. The sensor module includes a high linearity pressure sensor and an ultra-low power 24 bit ΔΣ ADC with internal factory calibrated coefficients. It provides a precise digital 24 Bit pressure and temperature value and different operation modes that allow the user to optimize for conversion speed and current consumption. The MS5803-01 BA can also be interfaced to many different microcontrollers.

The sensors may all be mounted on flexible PCBs.

Figure 10:
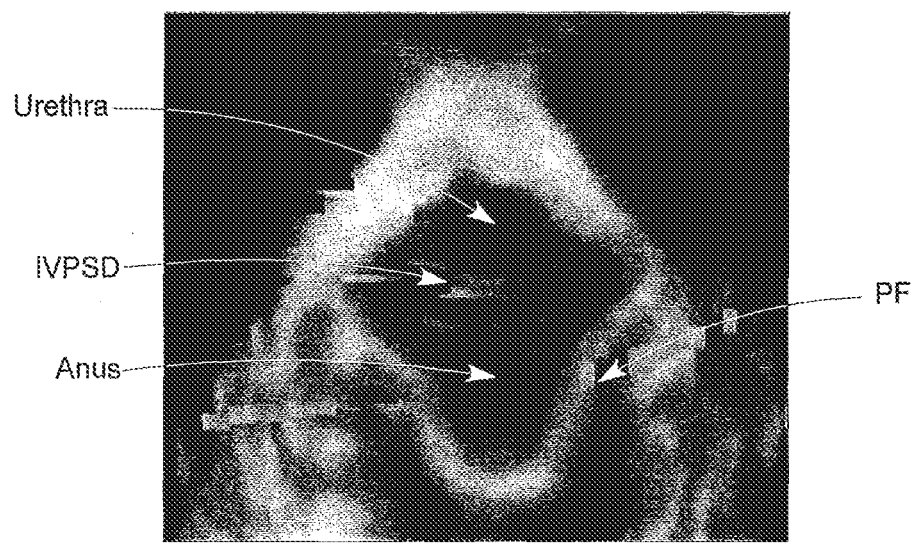
FIG. 10 shows an axial volume image of the human female pelvic floor with an inserted device according to an embodiment of the invention.

An assembled apparatus which includes the FIG. 7 embodiment is shown in FIG. 10. As shown in that figure, the substructure 1 of the apparatus has been moulded over or otherwise incorporated in a flexible biocompatible material to provide chambers 7, each of which contains a pressure sensing device 3. The retention contour in this embodiment comprises protruding regions 14, 15 which protrude transversely to the first (elongate or longitudinal) dimension along which the chambers 7 are provided. The retention contour may take other forms, for example a single protruding rib or wing may be present, and the protrusion could be at a different location. Also multiple ribs/wings may be provided at different angular locations. For example, two alternative embodiments of the pressure sensor apparatus are shown in FIG. 12. Here the retention contour is similar to that described above, but in 12(b) the protruding regions 110 are more like rectangular regions extending either side of the body 100 of the apparatus, In FIG. 12(a) the retention contour 120 comprises a plurality of ribs along the length of the body 130 on either side of the body.

The pressure sensor assembly may also be inserted into a detachable sheath. The sheath may provide protection from moisture ingress to the electronics and keep the pressure sensor assembly clean. The sheath may be supplied with different protruding regions 14, 15 of varying sizes to aid with retention. The sheath may be replaced every time the device is used, or on a regular basis. In the region of the pressure sensors, the sheath will be of a thin flexible material such as silicone rubber or latex.

The exit/funnel portion 16 guides conductors 21 (for example a data bus or FPC strip) out of the apparatus within a flexible tube 20 which may be constructed from a soft silicon material for example. The conductors 21 electrically connect the sensing devices 3 to an appropriate data transfer means. In one example this may comprises a transmission means such as a Bluetooth™ module for example. In other embodiments a transmission module may be proximal to the sensors (for example being moulded into a region adjacent to the sensor array). Various forms of communication may be used, for example Bluetooth, Zigbee or Wifi radio systems can be incorporated into the module 22. It will also be seen that in some embodiments the apparatus may include a memory to store data to be downloaded at a later time.

Transmission to a mobile device supports realtime feedback on the pressure profile during different conditions in the anatomical cavity in which the apparatus is located, for example during a pelvic floor exercise when the device is located in an intra-abdominal or intra-vaginal cavity. The access of the mobile device to the cloud allows feedback on performance compared to historical data and the sharing of outputs with other interested parties. Other interested parties include clinical and social users.

A clip will enable the module 22 to be attached to undergarments to secure the module during movement and exercise.

The apparatus may be used in the vagina to perform intra-abdominal pressure measurement. The materials and dimensions have been selected so that when in place the pressure sensor matches the contours of the vaginal wall. The pressure sensor of the present invention is a mobile intra-vaginal pressure sensing device (IVPSD), to continuously measure the vaginal pressure profile for evaluating the PFM performance. The information recorded from these sensors will be carried along an SRI bus exchange path 21, which will then be transmitted by a Bluetooth microcontroller 22 to a receiver or an app. Recorded pressures from the device are preferably sent via Bluetooth to an Android device, displayed by a user-friendly "app". However, other means of display may be used, for example, on any appropriate graphical user interface, PC or the like.

The pressure sensor of the present invention may be used to provide an extensive pressure profile along the vagina by incorporating approximately 6 sensors. The device can be used when a user is upright, walking or exercising.

Thus the present invention allows an array of measurements to be obtained along a pathway to provide a profile.

The profile gives information that quantifies the pressure that an individual can produce through squeezing their pelvic floor muscles. Properties derived from the profile, such as the gradient, enable patient status to be derived, and therefore the progression of their status when the measurement is obtained at a later time. The later time might be after a period of performing pelvic floor exercises, or after a period of professional treatment (e.g. physiotherapy or surgery).

The construction details presented show how two types of pressure sensors could be integrated into a flexible substrate that can be located in the vagina easily. The pockets and openings enable the identified sensors to respond to the pressure changes that will occur in the vagina during a range of activities. Other sensors may also be able to be used to quantify the pressure changes or at least provide a patient-specific baseline for the pressure profile in the vagina. The advantage of other sensors may be that the apparatus can be fabricated on a flexible printed circuit board and lower the production cost. An example of another sensor is the force transducer from TekScan, FlexiForce A201. Another example is a printed circuit trace where the resistance or capacitance changes when a surface above the trace moves closer due to compression from a pelvic floor muscle squeeze. These alternate sensors may not allow the derivation of the pressure along the vagina accurately, but may be sufficient to show the pelvic floor muscles are being contracted correctly to perform pelvic floor exercises.

The IVPSD has been tested and is shown in position in the ultrasound image of FIG. 10.

Figure 11:
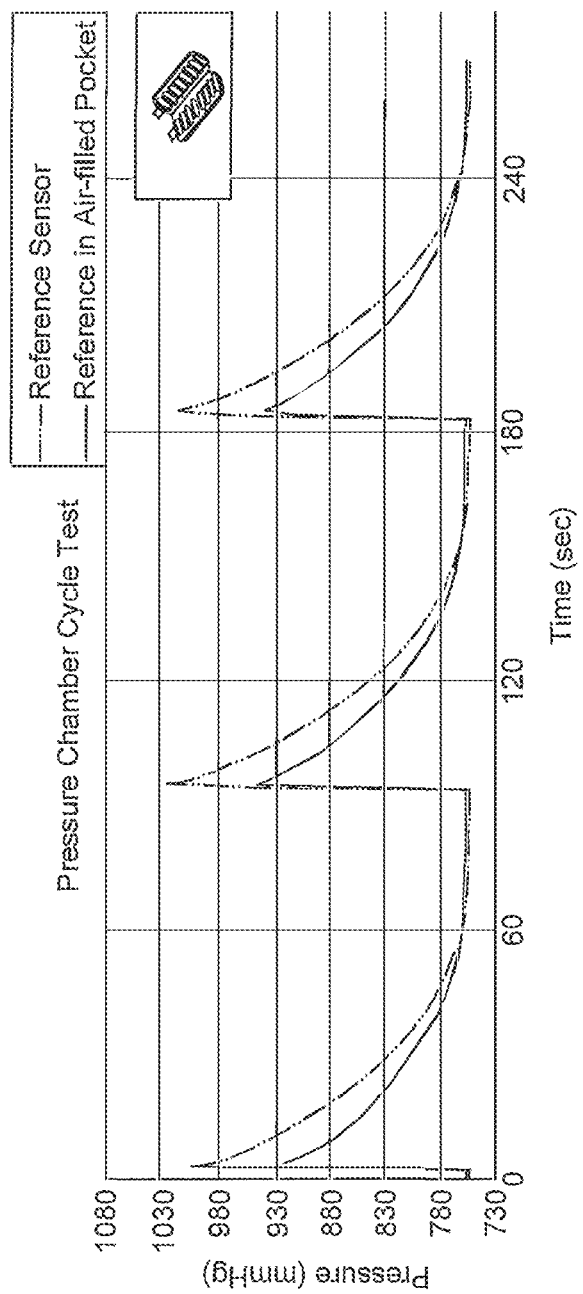
FIG. 11 is a plot showing the difference in pressure readings between a reference sensor in a fluid filled chamber and a sensor sitting in a membrane covered, air-filled pocket is not constant during pressure increase.

The use of individual fluid filled chambers that incorporate fluid pressure sensing devices provides superior performance to other constructions. When the sensors are covered by a membrane or contained within a pocket of compressible fluid, then the recorded pressure will be reduced compared to the pressure exerted on the outside surface of the membrane, as seen in FIG. 11. A calibration process is implemented to correct for the differences in pressure readings due to the encapsulation method used. The calibration method subjects the sensors to at least two known pressure levels.

Additionally, an IVPSD 200 as shown in FIG. 13, having an array of eight pressure sensors 230 (individually numbered 1 to 8) to enable measurement of the pressure along the length of a vagina, was tested on a number of different female human subjects.

The sensors 230 were mounted on a flexible printed circuit board 210 to allow the device to conform to the anatomy of the vagina, without distorting the vaginal walls. A soft biocompatible silicone (preferably MED-4901, NuSil, however, other appropriate materials may be used) was used as the encapsulating material or cover 220. In this embodiment, the array of sensors has a total length of 80 mm and a maximum width of 20 mm. The contoured edges cover a distance of 55 mm and are designed to sit within the rugae of the vaginal wall to reduce device movement. A lead 240 provides apparatus for data transfer from the flexible printed circuit board 210 that connects to further apparatus comprising in this example a small electronics module (not shown) which is located outside the human body. For preliminary testing, the IVPSD 200 was connected to an SPI bus (USB-8452, National Instruments) and a computer. LabVIEW served as the user-interface. Each pressure sensor sampled at a rate of 140 Hz.

Each subject knew how to contract their pelvic floor muscles and had no symptoms of POP. The IVPSD was self-inserted and the following tasks performed: maximum PFM contractions (3×5 s), as many as possible rapid PFM contractions (15 s), Valsalva (3×5 s) and coughing (5×). Vaginal pressures profiles were recorded for all tasks. Baseline pressures were recorded prior to each task. The raw data was analysed using MATLAB. For each task the maximum and mean pressures were calculated. For selected tasks the rate of pressure change was also computed.

Figure 14:
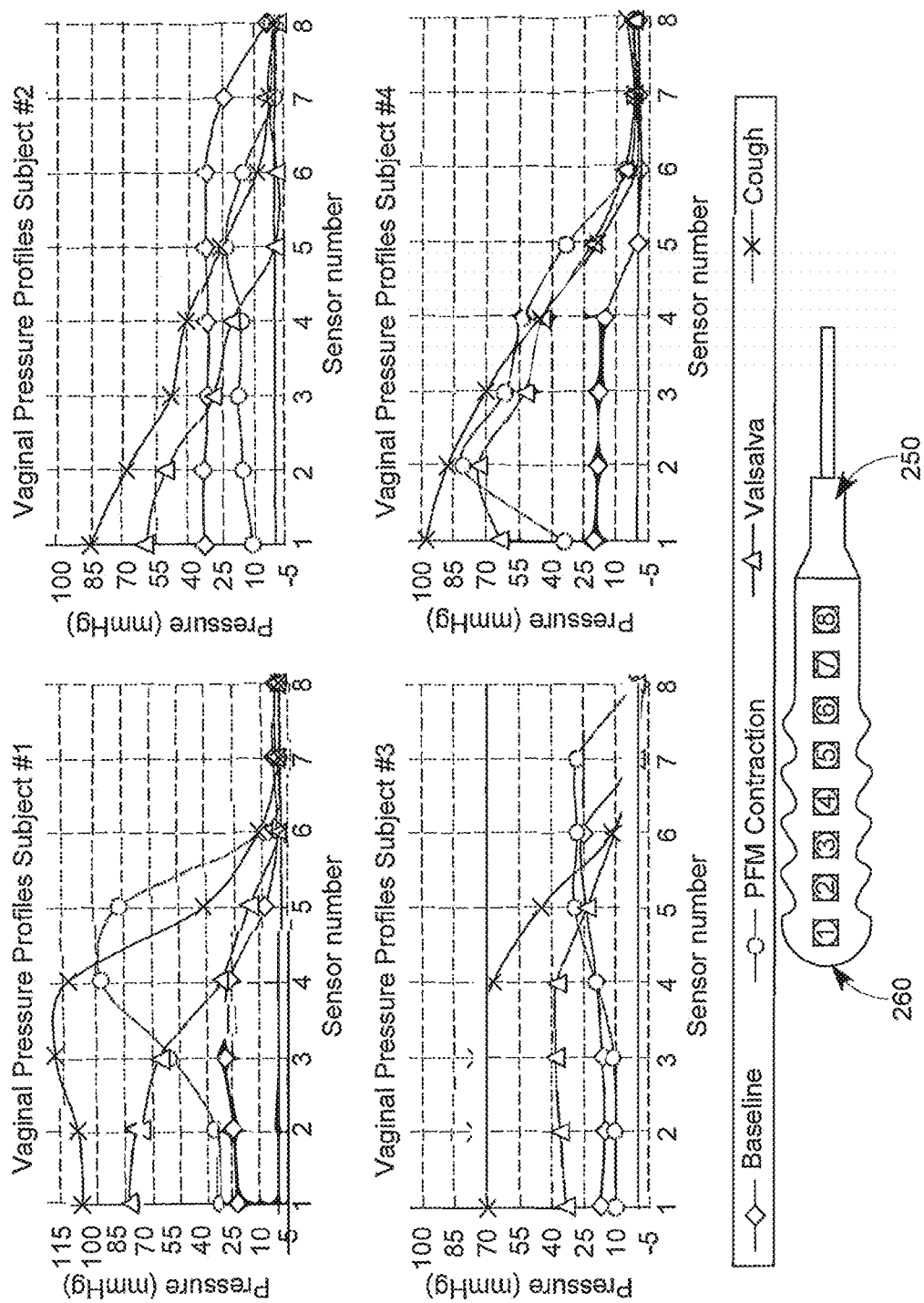
FIG. 14 shows pressure profiles for each of four subjects 1 to 4 using a pressure sensor apparatus also shown in FIG. 14.

The IVPSD has a tail 250 and a head 260, shown in FIGS. 13 and 14. The head 260 of the device sits in use in the deep vagina, and the sensors near the head measure abdominal pressure. The tail 250 of the device is located at the entrance of the vagina, the introitus.

Two of the subjects were vaginally parous and the other two were caesarean parous. The test subjects reported that the IVPSD was easy to insert and comfortable. Downward displacement of the IVPSD occurred only during cough or valsalva, more so in the vaginally parous women.

Pressure profiles for each of Subjects 1 to 4 are shown in FIG. 14. Atmospheric pressure has been subtracted for the baseline pressure. The baseline pressures have been subtracted from the profiles. Each resting baseline pressure profile was unique, although a drop in pressure in the region of the PFM was recorded for all subjects, reaching near atmospheric pressure at the introitus (see the illustration in FIG. 14 showing the position of the abdomen and introitus in relation to the device). Distinctive vaginal pressure profiles were measured for each task and each subject. During PFM contractions the greatest increase in pressure was in the region of the PFM, shown by the sensors placed approximately 3.5 cm from the introitus (for 3 out of the 4 subjects). Pressure increases ranged from 23 mmHg to 120 mmHg. Pressure profiles for cough and Valsalva showed the greatest pressure increase at the most distal sensors which would be measuring abdominal pressure. Maximum abdominal pressures were in the range of 70 mmHg to 120 mmHg for cough and 30 mmHg to 85 mmHg for Valsalva. The greatest rate of pressure change was 605 mmHg/s recorded for cough. Due to the small sample size, no statistical analysis could be performed.

The testing shows that the IVPSD is able to accurately measure the vaginal pressure profile and there are distinctive pressure profiles for the baseline and for each task. Evidence suggests that the IVPSD can capture the differences between abdominal pressure, PFM pressure and atmospheric pressure. In-vivo movement of the device needs to be accounted for, which may be done using signal processing or through changes to the physical shape design. A sampling frequency of 140 Hz was sufficient to capture rapid pressure changes, as experienced for coughing.

The testing also showed that the IVPSD is capable of simultaneous measurement of abdominal pressure and PFM pressure, producing a vaginal pressure profile, and has great potential for the IVPSD to be used as both an effective PFMT tool, and as an aid for clinician to define pre and post-surgical vaginal pressure profiles.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

The invention claimed is:

1. A pressure sensor apparatus comprising:
   an elongate body configured for anatomical cavity applications comprising a planar flexible substructure having a plurality of openings or pockets;
   at least one membrane molded directly to the planar flexible substructure and provided over each opening or pocket to provide a plurality of pressure responsive chambers provided successively along the elongate body;
   a pressure sensor device provided in each pressure responsive chamber;
   wherein each pressure responsive chamber comprises at least one pressure-transmitting wall formed by the at least one membrane, and the planar flexible substructure provides a pressure resistant barrier between adjacent chambers to mechanically isolate each of the plurality of pressure responsive chambers; and
   a data transfer apparatus configured to provide data from each pressure sensor device to allow simultaneous measurement of abdominal pressure and pelvic floor pressure.

2. The pressure sensor apparatus as claimed in claim 1 wherein the plurality of pressure responsive chambers is provided along a longitudinal dimension of the elongate body.

3. The pressure sensor apparatus as claimed in claim 1 wherein the pressure resistant barrier is sufficient to substantially prevent pressure changes in one chamber affecting pressure in the adjacent chamber.

4. The pressure sensor apparatus as claimed in claim 1 wherein each pressure responsive chamber is filled with a fluid whereby the pressure sensor device senses a pressure of the fluid in the pressure responsive chamber.

5. The pressure sensor apparatus as claimed in claim 4 wherein the fluid comprises air.

6. The pressure sensor apparatus as claimed in claim 1 wherein the data transfer apparatus provides a sensed pressure from each pressure sensor device to a display apparatus.

7. The pressure sensor apparatus as claimed in claim 6 wherein the data transfer apparatus comprises a transmitter.

8. The pressure sensor apparatus as claimed claim 1 further comprising a retention contour for retaining the apparatus in the anatomical cavity in use.

9. The pressure sensor apparatus as claimed in claim 8 wherein the retention contour extends substantially transversely.

10. The pressure sensor apparatus as claimed in claim 8 wherein the retention contour comprises one or more ribs or wings dependent from the elongate body.

11. The pressure sensor apparatus as claimed in claim 1 wherein the apparatus is used as an intra-abdominal pressure sensing device.

12. The pressure sensor apparatus as claimed in claim 1 wherein the apparatus is used as an intra-vaginal device.

13. The pressure sensor apparatus as claimed in claim 1 wherein the pressure sensor devices are mounted on a flexible printed circuit board.

14. The pressure sensor apparatus as claimed in claim 1 wherein the pressure sensor devices comprise an array and the array has a maximum width of 20 mm.

15. The pressure sensor apparatus as claimed in claim 1 wherein there are at least six pressure responsive chambers.

16. The pressure sensor apparatus as claimed in claim 1 wherein there are eight pressure responsive chambers.

17. A method for monitoring a female subject with a pelvic floor disorder comprising:
   (a) inserting into the subject's vagina a device comprising:
      an elongate body comprising a planar flexible substructure having a plurality of openings or pockets;
      at least one membrane molded directly to the planar flexible substructure and provided over each opening or pocket to provide a plurality of pressure responsive chambers provided successively along the elongate body, wherein each pressure responsive chamber comprises at least one pressure-transmitting wall formed by the at least one membrane, and the planar flexible substructure provides a pressure resistant barrier between adjacent chambers to mechanically isolate each of the plurality of pressure responsive chambers; and
      a pressure sensor provided in each pressure responsive chamber;
   (b) providing pressure data detected by the pressure sensors to a display device located exteriorly of the subject's vagina during performance of a pelvic floor exercise;
   (c) displaying on the display device a visual representation of the pressure data during the performance of the pelvic floor exercise by the subject.

18. The method of claim 17 further comprising (d) recording the pressure data.

19. The method of claim 18 further comprising using the pressure data to simultaneously measure or record abdominal pressure and pelvic floor pressure.

20. The method of claim 17 further comprising using the pressure data to simultaneously measure or record abdominal pressure and pelvic floor pressure.

21. The method of claim 17 further comprising providing biofeedback to the subject via the display device.

22. The method as claimed in claim 17 further comprising repeating steps (b) and (c).

23. The method as claimed in claim 17 further comprising performing the method under different conditions imposed on the subject's vagina.

* * * * *